United States Patent [19]

Fraser et al.

[11] Patent Number: 5,116,754
[45] Date of Patent: May 26, 1992

[54] SEPARATION OF BACTERIA FROM ORGANIC MATTER

[76] Inventors: Ann D. E. Fraser, 286D Dalehurst Drive, Nepean, Ontario, Canada, K2G 4E4; Dawn M. J. Martin, 13 Kingsmill Drive, Nepean, Ontario, Canada, K2E 5H9; Edward M. Riche, 2630 Draper Avenue, Ottawa, Ontario, Canada, K2H 8V2

[21] Appl. No.: 592,518

[22] Filed: Oct. 4, 1990

[51] Int. Cl.⁵ .......................... C12N 1/12; C12M 1/00
[52] U.S. Cl. ................................. 435/252.1; 435/261; 435/252.4; 435/287; 210/499; 210/609; 210/611
[58] Field of Search ................... 435/252.1, 252.4, 261, 435/803, 287; 210/499, 609, 611

[56] References Cited

U.S. PATENT DOCUMENTS

| | | | |
|---|---|---|---|
| 2,679,158 | 1/1951 | Claydon et al. | 73/61 |
| 3,668,925 | 6/1972 | Mesek | 73/61 R |
| 3,794,164 | 2/1974 | Ginaven | 210/499 |
| 4,290,888 | 9/1981 | Gartmann | 210/499 |

OTHER PUBLICATIONS

Amicon Product Catalog 1990 p. 43.
Truscott et al. J. Food Protection 50, No 10 pp. 815–819 1987.
Swaminathan et al., Rapid Detection of Salmonellae in Foods by Membrane Filter-Disc Immunoimmobilization Technique, (1978).
Truscott et al., Millipore Filtration and Use of RV Medium for Isolation of Salmonella from Preenrichment Broths, (1987).
Flowers, R. S., Comparison of Rapid Salmonella Screening Methods and the Conventional Culture Method.
Cox et al., A Comparison of Various Enrichment Broths and Plating Media for the Isolation of Salmonella from Poultry Feces and Poultry Food Products.
Cerqueira-Campos et al., Improved Immunological Membrane Filter Method for Detection of Food-Borne Salmonella Strains.

Primary Examiner—David M. Naff
Assistant Examiner—Jane Williams

[57] ABSTRACT

A method and a device for separating certain microorganisms from fecal matter are described. The method is effective in relatively fast detection and identification of bacterial pathogens in e.g. chicken feces, thus making it possible to diagnose certain diseases within a short period of time. The method comprises inducing the bacteria (microorganisms) containing matter through a sequence of basically non-absorbent screens with selected, gradually decreasing pore sizes. Factors important in optimizing the separation process are discussed.

15 Claims, 1 Drawing Sheet

SEPARATION OF BACTERIA FROM ORGANIC MATTER

FIELD OF THE INVENTION

This invention is concerned with separating bacteria from organic matter of biological origin, and more particularly, with the detection and identification of certain bacteria, e.g. pathogens, in human and animal feces or other similar media.

BACKGROUND OF THE INVENTION

The detection and identification of bacterial pathogens in human or animal feces is essential for the diagnosis of certain diseases. The speed with which these diagnoses are made is important. Rapid disease diagnosis could be a reality if it were possible to detect bacterial pathogens directly in fecal matter using immunologically based or nucleic acid based probes. Unfortunately, however, feces (fecal matter) constitute a rather complex mixture of lipids (fats), cellulosic fibres, proteins, microorganisms and water; in certain animal fecal matter, it is not uncommon to find gravel, feathers and other impurities. As a result, fecal matter is an example of a very difficult-to-separate organic matter. Extraneous components in the fecal matter interfere with the detection of bacteria by most probes such as nucleic acid or antibody probes, and obviously by microscope.

No method is known to be available for the separation of bacteria from fecal matter for direct detection by probes. Fecal samples are usually cultured on selective media which support the growth of the bacteria. The growth can take 16 hours or longer, making a same-day diagnosis unfeasible. The culturing of the fecal matter dilutes the extraneous components which would normally interfere with the detection of the bacteria by probes or culture methods.

Attempts have been made to separate bacteria from the above-mentioned organic matter by filtration using a single filtering layer, or a number of identical filtering layers. These attempts were unsuccessful as the filtering layers clog very quickly with fecal, or similar, matter.

U.S. Pat. No. 3,668,925 issued Jun. 13, 1972 to Mesek describes a method of detecting the existence of leucocytes in milk by passing the milk through a first filter which retains gross impurities present in the milk and through a finer filter of higher density. The filters are then separated along an interface therebetween. A discoloration of the second filter is indicative of a high leucocyte count in the milk.

Leucocytes, of course, are 10-20 times larger than bacteria. Milk is a very different medium than feces and its filtration poses much less difficulties than of the latter.

The most relevant literature on the subject includes:

1) Cerqueria-Campos, M.-L., et al, Improved Immunological Membrane Filtration Methods for Detection of Food-born Salmonella Strains, Applied and Environmental Microbiology 52: 124-127, 1986. This paper describes a membrane filter method that involves the use of an enzyme-labelled antibody stain for the rapid detection of salmonella species in foods. The method allows detection of salmonella in foods within 48 hours.

2) Cox, N. A., et al, A Comparison of Various Enrichment Broths and Plating Media for the Isolation of Salmonella from Poultry Feces and Poultry Food Products, Poultry Science L1: 1312-1316, 1972. This paper describes a study conducted to determine the efficacy of media prescribed by the FDA. A number of enrichment broths were tested. The experimental approach involved incubation, enrichment broth tubes were used to streak different plating media. The procedure takes more than 48 hours. There is a sizable percentage of false readings.

3) Flowers, R. S., Comparison of Rapid Salmonella Screening Methods and Conventional Culture Method, Outstanding symposia in Salmonella, 1984.

The author compares recently developed methods known as enzyme immunosorbent assays or enzyme immunoassays EIAs, and DNA-DNA hybridization assays with prior methods, fluorescent-antibody (FA) technique and Bacteriological Analytical Manual (BAM) culture procedure.

A common feature of all the above-mentioned methods, none of which is rapid enough to present reliable results in less time than ca. 16-24 hours, is that Salmonella is not physically separated from the solid matter, but rather enriched and subjected to a reaction with a specific detection agent.

SUMMARY OF THE INVENTION

It has been found unexpectedly that the separation of bacteria from fecal matter is possible, with a high degree of bacteria recovery when a method as described hereinbelow, in conjunction with a suitable device, is employed. The approach on which the method is based envisions fecal matter (or similar organic matter, e.g. certain foods) as a mixture of numerous solid fractions of various particle size. This assumption is in no way obvious when one considers the physical properties of fecal matter. However, in keeping with such assumption, it has been attempted successfully, according to the invention, to subject bacteria-containing fecal matter samples to sequential screening as opposed to filtering, the latter being concerned with separating a liquid filtrate from a solid retentate (solids retained on the filtering medium).

The bacteria-containing organic matter is therefore, according to the invention, subjected to separation into a number of portions by way of passing the matter through at least one sequence of screens with gradually decreasing pore sizes, the pore size of the last screen in the sequence selected so as to retain virtually all particles larger in size than the bacteria. The bacteria-containing undersize which is usually liquid and virtually free of other solids, may then be subjected to another separation step whereby the bacteria are isolated from the accompanying liquid.

It is preferable to apply pressure or vacuum to induce fecal matter to pass through appropriate screens.

Fecal matter, even diluted, is not likely to pass through micron-size screens, necessary for separation of bacteria, without a driving force.

Tests conducted to validate the invention have shown that while the selection of an optimum sequential screening set is largely a matter of experimenting in view of diversified character of the starting material, a number of guidelines can be established to facilitate the trial-and-error process. Thus, it is recommended that the sequence of screens is divided into at least two separate sets of screens, one set being a "continuation" of the other regarding the pore sizes. The division makes it easier to maintain the pressure on each screen at a substantially similar level as opposed to one continuous sequence where, due to the gradual pressure drop across the screens during the operation, the pressure on the last screen(s) would be relatively very low resulting in the clogging of that screen or screens. On the other hand, it would be impractical to provide a large number of sets for economic reasons. Two or three sets, each comprising 2-5 layers, have been found satisfactory.

Further, it is preferable to select a sequence of screen pore sizes such that the pressure drop on each screen in the set (sequence) is approximately similar during the screening operation. This results, according to our experiments, in the retention of similar or gradually smaller amounts of solids on the consecutive screens while clogging is avoided to a substantial degree.

The invention will be described in more detail by the following description of its preferred embodiments.

DETAILED DESCRIPTION OF THE INVENTION

Figure 1:
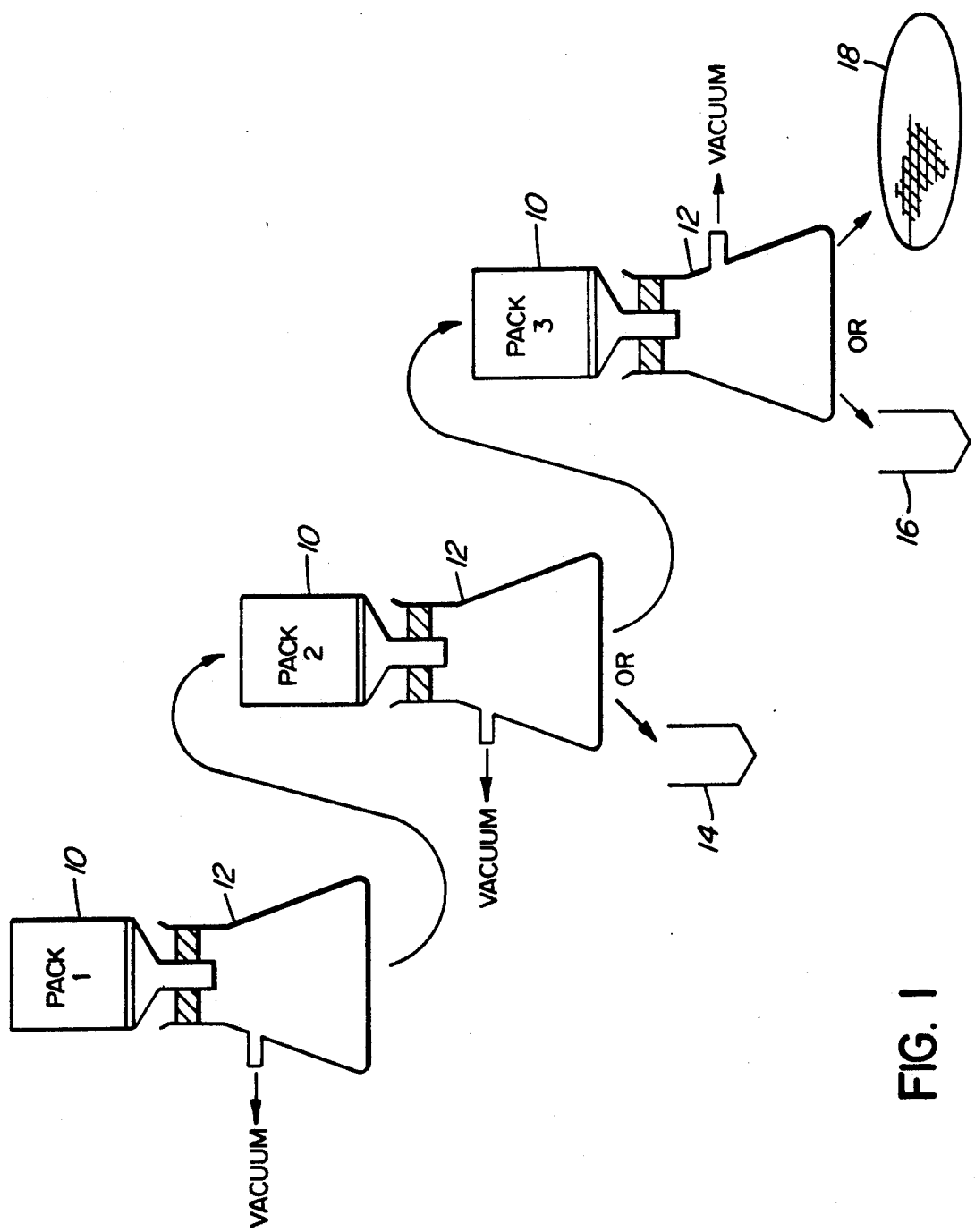
FIG. 1 is a schematic illustration of the screening device of the invention.

In the embodiment illustrated in the drawing, three sets (packs) of screens are provided for separating and detecting Salmonella in chicken feces. The three packs are installed in 9 cm. dia. plastic funnels 10 equipped with plastic support screens. The funnels are each installed in a vacuum container 12. Packs #1 and #2 are designed to retain virtually all the solid matter of the feces while bacteria, including Salmonella, and an amount of liquid from the sample pass through first and second pack and become partially filtered on pack #3. The filtrate, or "undersize" from pack #2 may be centrifuged to separate a bacterial "cake" from the liquid, using a centrifuge tube 14. Alternatively, a bacteria-specific pack #3 may be employed to separate certain bacteria from the filtrate. For instance, gram-positive bacteria may be trapped within the pack #3 possibly due to size and cell wall factors, while gram-negative bacteria and liquid will pass therethrough. The filtrate of pack #3 may then be centrifuged in a centrifuge tube 16 to isolate bacteria from the liquid or the same result may be achieved by using a bacteria capturing membrane filter 18. An exemplary sequence of screens as described below was found satisfactory for the above-mentioned Salmonella separation.

| Layer | Material |
|---|---|
| Pack 1 (separation of coarse matter) | |
| 1. | Nylon screen, 52 $\mu$m opening, 70 $\mu$m thick, 33% open area. |
| 2. | Nylon screen, 20 $\mu$m opening, 60 $\mu$m thick, 16% open area. |
| 3. | Polypropylene separator, 127 $\mu$m thick. |
| 4. | Paper, retention 20-25 $\mu$m 220 $\mu$m thick, weight 75 gm/m$^2$, high wet strength. |
| 5. | Same as 3. |
| 6. | Paper, retention 20-25 $\mu$m, 210 $\mu$m thick, weight 92 gm/m$^2$, low wet strength. |

The commercial specification of the above layers is:
1—Spectra/Mesh Nylon N 145914
2—Spectra/Mesh Nylon N 145920
3—Gelman 61795 (cut to size)
4—Whatman #114
5—Gelman 61795
6—Whatman #4.

| Layer | Material | |
|---|---|---|
| Pack 2 (separation of remaining intermediate and fine solids) | | |
| 1 | Paper, retention size 11 $\mu$m, 180 $\mu$m thick, weight 87 gm/m$^2$, low wet strength. | Whatman #1 |
| 2. | Nylon screen, 10 $\mu$m opening, 45 $\mu$m thick, 5% open area. | Spectra/Mesh Nylon N 145922 |
| 3. | Paper, retention size 7 $\mu$m,-170 $\mu$m thick, weight 98 gm/m$^2$, high wet strength. | Whatman #52 |
| 4. | Nylon screen, 1 $\mu$m opening, 80 $\mu$m thick, 0.75% open area. | Spectra/Mesh Nylon N 145924 |
| Pack 3 (enterobacteria specific filter) | | |
| | Contains 10 layers of borosilicate microfibre glass with acrylic resin binder. The glass microfibre layers have a density 0.16 g/cm$^3$ and thickness 1.25 mm. each. Membrane filters for capturing bacteria which pass through pack 3. Pore sizes 0.45, 0.65 and 0.8 $\mu$m have been found adequate. | Micropore AP 25 |

The above described screening set-up and the particular selection of screening layers have been determined by trial-and-error combined with the basic knowledge of filtering/screening principles. The basic assumption which lay the groundwork for the success of the approach was that the organic matter in question—feces, food, extracts, etc. will not separate from the bacteria in one filtering step despite a clear span between the size of bacterial cells and the smallest interfering solid organic matter particles. Any single filter will clog with such organic matter with the microorganisms trapped therein. On the contrary, an attempt should be made to select a screen which will pass relatively fast—with a time period in the range of 0.5-10 minutes—from about 1% to 10% by weight of the starting material. A number of remarks is applicable in this respect.

First, as mentioned hereinabove, the physical properties, in particular density, moisture content, viscosity and composition of various organic materials of interest may vary widely; poultry feces, for example, is very different from e.g. a carcass rinse. It would be desirable to bring all materials tested to an optimum consistency by a standard method to be able to use a small number of devices, preferably only one, instead of a large number thereof, each tailored for a particular organic matter. One way of bringing the starting material, e.g. fecal matter, to an optimum, standard consistency, is to homogenize the sample in an aqueous solution of a salt at room temperature or elevated temperature (ca 40° C.). A standard saline solution is sufficient.

Secondly, it is advantageous to wash the solids obtained on the screens with an excess amount of the same aqueous salt solution. This has been found to increase markedly the final recovery of bacteria from the sample.

Thirdly, it is desirable to use screens as opposed to depth filters, to separate bacteria and liquid from the remaining solid organic matter. For example, tests conducted within the scope of this invention demonstrated that paper filters are capable of retaining some fecal solid matter while passing through smaller size material. However, the paper layers tend to accumulate some amounts of the "undersize" material in the bulk of cellulosic fibres thus reducing the efficiency of the device somewhat. It can be concluded that an optimum screening set-up should contain non-absorbent (polymer, metal) sieves only, non-woven polymer fabric being preferred over woven one.

Certain organic materials that may be subject to testing may also contain mucus. This would likely be the case for bovine fecal matter. The mucus content is likely to interfere with even best-designed screening procedure and device according to the invention. In order to alleviate the mucus-related clogging of the screening layers, a mucolytic agent e.g. N-acetyl-l-cysteine should be added to the starting material, and preferably also to the washing liquid. The concentration of the agent should be selected so as not to interfere with (destroy) the bacterial flora to be isolated. Recommended concentration of the above-mentioned agent could be about 0.05% by weight.

Exemplary Screening Method

A set-up as described above was used. Polypropylene separators were used to separate paper filters from each other and from the polymeric screens to reduce the depth filter effects. The diameter of screens in pack #1 and pack #2 was 9 cm. Vacuum was applied by means of a typical laboratory vacuum system.

A 10 g chicken feces sample was homogenized in 100 ml. 0.8% saline at room temperature using a "stomacher" for ca. 1 minute. The sample was then passed through pack #1 and chased (washed) with another 100 ml of the saline. The "undersize" was passed through the pack #2 and washed similarly as with pack #1. The procedure yielded an almost colourless liquid which was passed through pack #3 and washed with 100 ml. saline as well. The filtrate of pack #3 was filtered through a membrane filter. Membrane filters with pore sizes 0.45, 0.65 and 0.8 $\mu$m were tried interchangeably and all of them were effective in capturing virtually all Salmonella present.

In the actual experiments, when the separation of gram-positive bacteria from gram negative ones was intended the pack #3 consisted of 10 borosilicate layers. However, to obtain different microbial profiles, fewer layers (e.g. 2 or 3) may be used. The microfibre glass layers of pack #3 work as a depth filter.

As illustrated schematically in the drawing, the two sets (packs) of screens, pack #1 and pack #2 are the first step in separating bacteria-containing liquid mass, substantially free of interfering non-bacterial solids, from the latter. Depending on the selected analytical approach, further procedure may involve centrifugation (centrifuge tube 14) to separate the filtrate of pack #2 into a bacterial mass and a liquid phase. Alternatively, the filtrate may be passed through a number of layers of the pack #3. The filtrate of pack #3 may further be separated into a solid phase (bacteria) and a liquid phase.

The optimum screening sequence of the invention was effective to separate most of bacteria, including Salmonella, from the organic non-bacterial solid matter of a 10 g chicken feces sample within ca. 15 min using the dilution and washing steps as described hereinabove. It will be appreciated that the efficiency of any filtering or screening device must be related to the surface of the screening/filtering layers. The larger the surface, the faster the filtering/screening process. However, for laboratory purposes and because of economic considerations, the device should not be excessively large. For the purposes of fast analysis of Salmonella in organic matter as explained above, where samples of ca. 10 g are quite sufficient, the device of the present invention may use ca. 9 cm. dia. screens.

Such device, when manufactured from inexpensive plastics, e.g. polyethylene or polypropylene, and when comprising polyamide screens only, may be used as a disposable device, including the microfibre glass pack #3.

It will also be appreciated that fecal matter is one of the most difficult-to-separate media of interest to bacteriologists. More homogeneous, less viscous and more diluted media, e.g. milk or carcass rinses, may easily be dealt with using the device of the invention, and it may be possible to achieve good separation of bacteria with pack #2 only.

It must be emphasized that the selection of pore sizes of consecutive screens and the number thereof is always a matter of optimizing choice; the present tests were conducted only with filters available on the market. It can only be speculated, therefore, that the optimum sequence of screens should form an exponential series. This assumption was supported by the finding that when 50 $\mu$m mesh was used as the first screen, and 20 $\mu$m layer was successful as the second one, a "jump" from 20 $\mu$m to 10 $\mu$m was not possible. As no screen sizes between 20 and 10 $\mu$m were available, paper layers were selected as shown hereinabove.

In the case of fecal matter, it was found that the mesh of the first screen is very important. Screens with pore size in the range about 40–55 were effective in screening about 90–98% of the chicken fecal matter diluted with a saline solution, as described hereinabove. Through the addition of a mucolytic agent, bovine fecal matter has been found amenable to screening from microorganisms as well. Soil can also be separated from microorganisms relatively easily using the method and apparatus of the invention.

We claim:

1. A method of separating viable bacteria from bacteria-containing organic matter, or mixtures thereof with inorganic matter, the method comprising the steps of:
   (a) admixing said organic matter with saline solution;
   (b) generating a first filtrate by inducing said organic matter and saline solution to pass through a first filter pack, wherein said first filter pack comprises a set of stacked filter members, the pore size of each sequentially decreasing from the first to the last;
   (c) washing said first filter with a saline solution and mixing the wash therefrom with said first filtrate;
   (d) generating a second filtrate by inducing said first filtrate and wash to pass through a second filter pack wherein said second filter pack comprises a set of stacked filter members the pore size of each sequentially decreasing from the first to last and the pore size of the first is smaller than the last filter member in the first filter member, and the pore size of the last filter member is larger than the bacteria;
   (e) washing said second filter with a saline solution and mixing the wash therefrom with said second filtrate;
   (f) generating a third filtrate by inducing said second filtrate and wash to pass through a third filter pack comprising one or more layers of borosilicate microfibers;
   (g) washing said third filter with a saline solution and mixing the wash therefrom with said third filtrate; and (h) separating said bacteria from said third filtrate and wash.

2. The method according to claim 1 wherein the bacteria-containing matter is induced to pass through said first, second and third filter packs under positive or negative pressure.

3. The method according to claim 1 wherein the bacteria-containing matter is a fecal matter and the first filter member of said first filter pack has a pore size in the range about 55-40 μm and is capable of retaining about 90-98% by weight of the solids of said matter.

4. The method according to claim 1 wherein N-acetyl-1-cysteine is added to the bacteria-containing matter before or during the filtering.

5. A device for separating viable bacteria from bacteria-containing organic matter or mixtures thereof with inorganic matter, the device comprising: a first filtering means including a first holder, a first filter pack having a set of stacked filter members in said holder, said filter member within said set having sequentially decreasing pore size from the first to the last and vacuum means to induce said organic matter to pass through said first filtering means; second filtering means including a second holder, a second filter pack having a set of stacked filter members in said second holder, said filter members within said set having sequentially decreasing pore size from the first to the last, the pore size of the first being smaller than the pore size of the last filter in the first pack and larger than said bacteria, and vacuum means to induce material having passed through said first filter means to pass through said second filter, a third filter means having a third holder, a filter comprising at least one layer of borosilicate microfibers, and vacuum means to induce material having passed through the second filter to pass through said third filter and means to separate said bacteria from material having passed through said third filter means.

6. The device according to claim 5 where the pore sizes of the consecutive filters are selected to cause a substantially similar pressure drop at each filter during the matter being passed through the sequence of filters.

7. The device according to claim 5 wherein the pore size of the last filter is in the range 0.8-2.0 μm.

8. The method of claim 1 wherein said step of separating said bacteria comprises centrifuging said third filtrate and wash to produce a bacteria pellet.

9. The method of claim 1 wherein said bacteria is separated by passing said third filtrate and wash through a membrane filter having a pore size adapted to retain said bacteria thereon.

10. The method of claim 1 wherein said organic matter is chicken feces.

11. The method of claim 1 wherein said bacteria is Salmonella.

12. The method of claim 1 wherein said bacteria is Campylobacter.

13. The device of claim 5 wherein said means to separate bacteria comprises a centrifuge.

14. The device of claim 5 wherein said means to separate bacteria comprises a membrane filter having a pore size adapted to retain said bacteria thereon.

15. The device of claim 5 wherein the pore size of said set of filters in said first filter pack range from 52 μm to 20 μm and the pore size of said set of filters in said second filter pack range from 11 μm to 1 μm.

* * * * *